(12) United States Patent
Wiemker et al.

(10) Patent No.: US 8,107,707 B2
(45) Date of Patent: Jan. 31, 2012

(54) VISUALIZING A VASCULAR STRUCTURE

(75) Inventors: Rafael Wiemker, Kisdorf (DE); Roland Opfer, Hamburg (DE); Thomas Buelow, Grosshansdorf (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 422 days.

(21) Appl. No.: 12/516,670

(22) PCT Filed: Nov. 27, 2007

(86) PCT No.: PCT/IB2007/054807
§ 371 (c)(1),
(2), (4) Date: May 28, 2009

(87) PCT Pub. No.: WO2008/065611
PCT Pub. Date: Jun. 5, 2008

(65) Prior Publication Data
US 2010/0074493 A1 Mar. 25, 2010

(30) Foreign Application Priority Data
Nov. 30, 2006 (EP) .................... 06125074

(51) Int. Cl.
*G06K 9/00* (2006.01)
(52) U.S. Cl. ........ 382/130; 382/128; 382/131; 600/425; 600/481
(58) Field of Classification Search .......... 382/128–134, 382/164, 171, 173, 177; 600/407, 415, 419, 600/480–482, 381, 425; 345/424, 419, 420, 345/422; 703/2, 6; 378/4, 6, 8, 901
See application file for complete search history.

(56) References Cited

U.S. PATENT DOCUMENTS

| | | | | |
|---|---|---|---|---|
| 5,978,439 A * | 11/1999 | Koppe et al. | ...................... | 378/8 |
| 6,842,638 B1 * | 1/2005 | Suri et al. | ...................... | 600/425 |
| 6,975,973 B1 * | 12/2005 | Bruijns | ...................... | 703/2 |
| 7,274,810 B2 * | 9/2007 | Reeves et al. | ...................... | 382/128 |
| 7,397,937 B2 * | 7/2008 | Schneider et al. | ............ | 382/130 |

(Continued)

FOREIGN PATENT DOCUMENTS
WO  2006042322 A1  4/2006

OTHER PUBLICATIONS

Aylward, S. R., et al.; Initialization, Noise, Singularities, and Scale in Height Ridge Traversal for Tubular Object Centerline Extraction; 2002; IEEE Trans. on Medical Imaging; 21(2)61-75.

(Continued)

*Primary Examiner* — Sang Nguyen

(57) ABSTRACT

A system (500) for visualizing a vascular structure represented by a three-dimensional angiography dataset is disclosed. Respective voxel values are associated with respective voxels. The dataset represents a vascular structure. The system comprises means (502) for establishing respective filling values; means (504) for identifying respective minimum filling values; means (506) for computing respective deficiency values; and an output (514) for providing a visualization in dependence on the deficiency values. A respective filling value is indicative of an amount of blood flow at the respective position in the vascular structure. A respective minimum filling value is a minimum of the filling values associated with the positions upstream of the respective position. A respective deficiency value is indicative of a difference between the filling value associated with the respective position and the minimum filling value associated with the respective position.

8 Claims, 5 Drawing Sheets

U.S. PATENT DOCUMENTS

| | | | |
|---|---|---|---|
| 7,903,113 B2 * | 3/2011 | Krishnan et al. | 345/424 |
| 2002/0114503 A1 | 8/2002 | Klotz et al. | |
| 2003/0099386 A1 | 5/2003 | Schneider et al. | |
| 2005/0240094 A1 | 10/2005 | Pichon et al. | |

OTHER PUBLICATIONS

Kiraly, A. P., et al.; Analysis of arterial sub-trees affected by Pulmonary Emboli; 2004; Medical Imaging-Image Processing; SPIE; vol. 5370:1720-1729.

Pichon, E., et al.; A novel method for pulmonary emboli visualization from high-resolution CT images; 2004; Medical Imaging-Visualization; SPIE; vol. 5367:161-170.

Brieva, J., et al.; Coronary Extraction and Stenosis Quantification in X-ray Angiographic Imaging; 2004; IEEE Trans. on EMBS; pp. 1714-1717.

Hernandez-Hoyos, M., et al.; Computer-assisted Analysis of Three-dimensional MR Angiograms; 2002; RadioGraphics; 22:421-436.

Kiraly, A. P., et al.; Analysis of arterial sub-trees affected by Pulmonary Emboli; 2004; Proc. of SPIE-Medical Imaging; vol. 5370:1720-1729.

* cited by examiner

“A novel method for pulmonary emboli visualization from high-resolution CT images”, by Pichon, Novak, Kiraly, and Naidich, in Proc. SPIE Medical Imaging 2004, describes a method to highlight potential PEs on a 3D representation of the pulmonary arterial tree. First lung vessels are segmented using mathematical morphology techniques. The density values inside the vessels are then used to color the outside of a shaded surface display of the vessel tree. As PEs are clots of significantly lower Hounsfield unit values than surrounding contrast-enhanced blood, they appear as salient contrasted patches in this 3D rendering.

VISUALIZING A VASCULAR STRUCTURE

FIELD OF THE INVENTION

The invention relates to visualizing a vascular structure, in particular a vascular structure represented by a three-dimensional angiography dataset in which respective voxel values are associated with respective voxels.

BACKGROUND OF THE INVENTION

Pulmonary embolisms (PE) are a potentially lethal lung disease relating to clots in the pulmonary arteries. These clots hinder the passage of blood through the artery, which may result in an insufficient perfusion of the arterial vessel tree of the lung. The clots can be observed in high resolution CT volume images, because the absence of contrast agent in the clots results in lower Hounsfield values.

"A novel method for pulmonary emboli visualization from high-resolution CT images", by Pichon, Novak, Kiraly, and Naidich, in Proc. SPIE Medical Imaging 2004, describes a method to highlight potential PEs on a 3D representation of the pulmonary arterial tree. First lung vessels are segmented using mathematical morphology techniques. The density values inside the vessels are then used to color the outside of a shaded surface display of the vessel tree. As PEs are clots of significantly lower Hounsfield unit values than surrounding contrast-enhanced blood, they appear as salient contrasted patches in this 3D rendering.

"Analysis of arterial sub-trees affected by pulmonary emboli", by Kiraly, Pichon, Naidich, and Novak, in Proc. SPIE Medical Imaging 2004, proposes a method to compute characteristics of the local arterial tree given the location of a PE. The computed information localizes the portion of the arterial tree that is affected by the embolism. The method is based on the segmentation of the arteries and veins followed by a localized tree computation at the given site. The method determines bifurcation points and the remaining arterial tree. The document also discloses assessing the affected lung volume and arterial supply.

SUMMARY OF THE INVENTION

It would be advantageous to have an improved way of visualizing an angiographic dataset. To better address this concern, in a first aspect of the invention a system is presented that comprises:

means (502) for establishing respective filling values (314), based on the voxel values, associated with respective positions in the vascular structure, a respective filling value being indicative of an amount of blood in a neighborhood of the respective position in the vascular structure;

means (504) for determining respective minimum filling values (316) associated with the respective positions in the vascular structure, a respective minimum filling value being a minimum of the filling values (314) associated with the positions upstream of the respective position;

means (506) for computing respective deficiency values (318) associated with the respective positions in the vascular structure, a respective deficiency value being computed in dependence on the filling value (314) associated with the respective position and the minimum filling value (316) associated with the respective position; and an output (514) for providing a visualization (408) in dependence on the deficiency values.

A lesion, such as an embolism, in an artery can be characterized by a local minimum in the filling values along a vessel. For a given position along the vascular structure, the system establishes the filling value as well as a minimum of filling values associated with positions upstream of the given position. The system also computes the deficiency value in dependence on the filling value and the minimum filling value. For example, a difference between the two values or a ratio of the two values is used as the deficiency value. Normally, because of the gradual narrowing of vessels and because the blood is distributed among branches, the filling values will gradually decline in downstream direction. Because of this, the minimum filling value is a filling value associated with a position near the given position, and has a value close to the filling value. However, since the lesion is characterized by a local minimum in the filling values, the filling values of a portion of the vascular structure downstream of the lesion will not be close to the minimum filling value, and the deficiency value may be used as an indication of a severity of the lesion. The visualization in dependence on the deficiency values provides more insight in the potential severity of the lesion. It shows how the lesion affects the flow of blood to the positions for which the deficiency value has been computed. This allows a relatively information rich visualization of the vascular tree.

The voxel values may by measured using a medical imaging device such as CT or MRI. Depending on the type of angiographic acquisition, the acquisition may be performed in combination with an intravenous or intra-arterial contrast agent injection. In this case, the voxel values may be responsive to a concentration of contrast agent at the associated voxel locations. The voxel values may also be responsive to for example an amount of fluid flowing to the voxel location. The filling values may be established in many different ways. For example, the voxel values associated with voxels at a centerline of a vessel of the vascular structure may be used as the filling values. The neighborhood may have a predefined shape and size, for example the neighborhood may include one or a few voxels around the position, or it may include voxels in a vessel cross section. The average of voxel values associated with voxels in a cross section of a vessel of the vascular structure may also be used as the filling value. The diameter of the cross section may also be used. The vascular structure may for example be a pulmonary arterial tree, possibly containing one or more pulmonary embolisms. It may be any arterial or venous system in the body, for example an intracranial vessel structure. The minimum filling values are a minimum of the filling values associated with upstream positions. Here, 'upstream' refers to the flow of blood, i.e. upstream positions include positions from where blood flows to the position associated with the minimum filling value. The positions for which the filling values, minimum filling values, and deficiency values are computed, may include for example all voxel locations along vessel centerlines of the vascular structure. A subset of all these voxel locations can also be used. It is also possible, for example, that the filling value is computed for more positions than the minimum filling value and/or the deficiency value.

According to an aspect of the invention, the means for establishing the respective filling values comprises:

means (516) for computing a generalized distance map in which respective generalized distance values based on the voxel values are associated with respective voxels; and means (518) for establishing a vessel centerline in dependence on the generalized distance map or in dependence on the voxel values;

means (520) for establishing the respective filling values in dependence on the respective generalized distance values associated with the respective voxels at the vessel centerline.

The filling values thus computed combine information about the diameter of the vessel cross section and the voxel values associated with the voxels in the vessel cross section. This combined information provides deficiency values that more accurately indicate the lesion severity.

The generalized distance map is known from "Morphological image analysis" by P. Soille, Springer-Verlag, Berlin, 1999, referred to hereinafter as "Soille". In one example of a generalized distance map, generalized distance values are computed as a smallest possible result of integrating (or adding up) the voxel values on a path from the background to the respective voxel. Here, the background consists of voxels outside the vascular structure, for example, voxels not reached by the contrast agent. Mathematically, background voxels may be defined as voxels having a voxel value below a predefined threshold value. Other definitions of the background may also be used. Instead of integration, other functions may be used such as counting the number of voxels on the path or averaging the voxel values of voxels on the path.

According to an aspect of the invention, the means for establishing the vessel centerline:

comprises means for identifying a plurality of voxels on a crest line of the generalized distance map or of the voxel values; and is arranged for using the plurality of voxels as the vessel centerline.

This is a particularly efficient way of computing the vessel centerline.

According to an aspect of the invention, the voxel values are indicative of a local concentration of contrast agent, and the means for establishing the respective filling values is arranged for computing the respective filling value as an estimate of a degree of local contrast agent filling in a cross section of the vessel at the respective position in the vascular structure.

According to an aspect of the invention, the means for identifying respective minimum filling values comprises means for establishing the positions upstream of the respective position by identifying positions along the vascular structure between the respective position and a predefined inflow point of the vascular structure.

By defining an inflow point of the vascular structure, efficient known algorithms can be used to compute a path between the inflow point and the position. This way the upstream portion of the vascular structure is efficiently established.

According to an aspect of the invention, the means for computing the respective deficiency values is arranged for computing the respective deficiency value in dependence on a difference between the filling value associated with the respective position and the minimum filling value associated with the respective position.

The difference is a particularly suitable indication of the deficiency.

An aspect of the invention comprises a rendering means (508) for rendering the three-dimensional dataset on a display in dependence on the computed deficiency values, the rendering means comprising:

a storage for storing a mapping (522) associating respective deficiency values with respective rendering parameters;

means (524) for applying the parameters according to the mapping and the deficiency values.

The rendering parameters may be indicative of at least one of: a color, a brightness, a gray value, or a texture. By applying the parameters when rendering the cross section, the potentially endangered portion(s) of the vascular structure may be observed more clearly.

An aspect of the invention comprises a method of visualizing a vascular structure (306) represented by a three-dimensional dataset in which respective voxel values are associated with respective voxels, the method comprising:

establishing respective filling values (314), based on the voxel values, associated with respective positions in the vascular structure, a respective filling value being indicative of an amount of blood in a neighborhood of the respective position in the vascular structure;

determining respective minimum filling values (316) associated with the respective positions in the vascular structure, a respective minimum filling value being a minimum of the filling values (314) associated with the positions upstream of the respective position;

computing respective deficiency values (318) associated with the respective positions in the vascular structure, a respective deficiency value being computed in dependence on the filling value (314) associated with the respective position and the minimum filling value (316) associated with the respective position; and providing a visualization (408) in dependence on the deficiency values.

BRIEF DESCRIPTION OF THE DRAWINGS

These and other aspects of the invention will be further elucidated and described with reference to the drawing, in which.

DETAILED DESCRIPTION OF EMBODIMENTS

Figure 1:
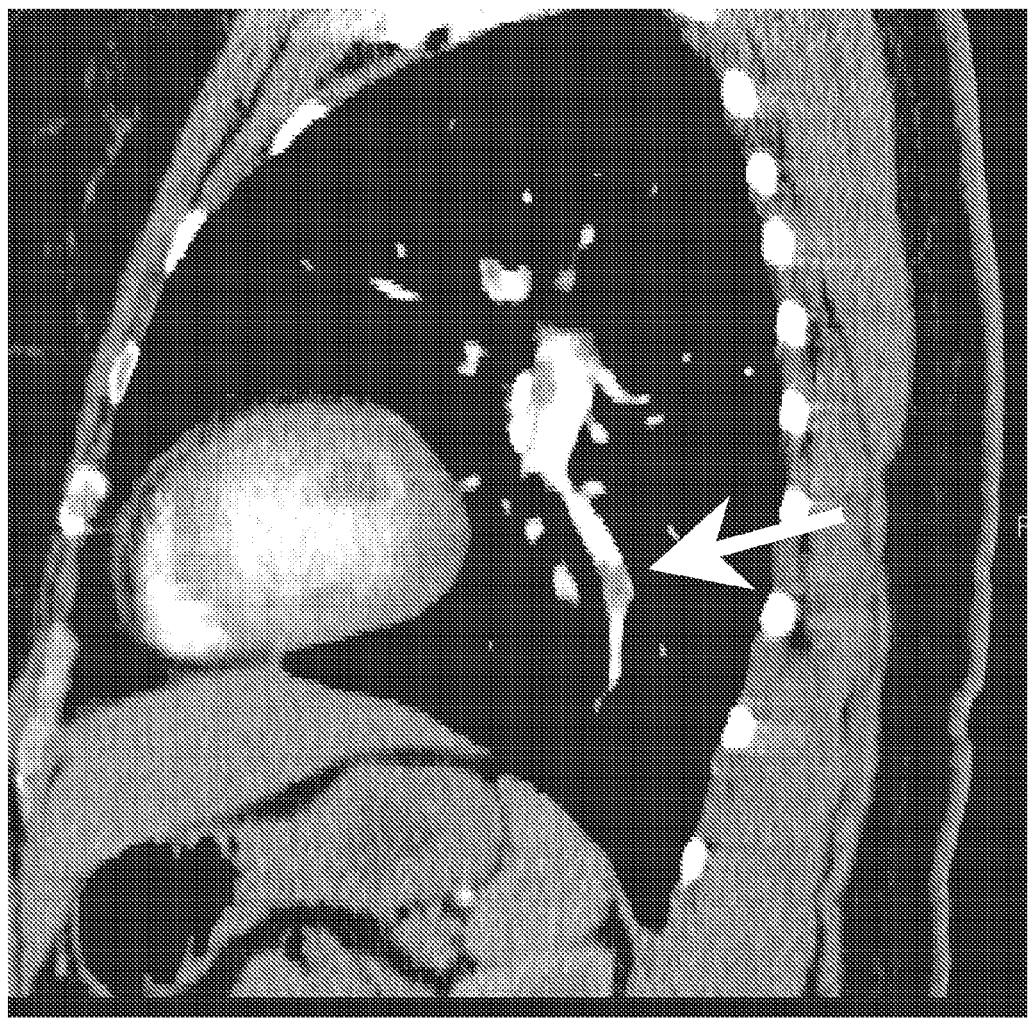
FIG. 1 shows an example CT image of a pulmonary embolism.

Pulmonary embolisms (PE) are a potentially lethal lung disease relating to clots in the pulmonary arteries. These clots hinder the passage of blood through the artery, which may result in an insufficient perfusion of the arterial vessel tree of the lung. The clots can be observed in high resolution CT volume images, because the absence of contrast agent in the clots results in lower Hounsfield values. For example, FIG. 1 shows a CT slice. The white arrow in the Figure is pointing to a PE. Visual inspection of the lung vessels in the original CT slice images for the detection of clots in the arteries is often tedious and time consuming. The filling defects caused by the clots can be easily overlooked. Moreover it is difficult to quantify the effect of a filling defect on the overall lung vessel tree by visual inspection of the CT images.

Embolisms also occur in other arteries, including intracranial arteries and coronary arteries. They can also be observed in medical images obtained from other modalities, such as magnetic resonance (MR) angiography. What is described herein in particular relating to the example of pulmonary embolisms using CT images may also be applied to embolisms elsewhere in the body and/or using images obtained from different types of imaging modalities.

The following describes ways to automatically visualize and highlight the location of embolisms and the affected vessels for convenient interactive inspection by, for example, a physician.

The embodiments can be implemented by means of a software component of a (CT) scanner console, an imaging workstation (such as ViewForum or Extended Brilliance Workspace from Philips Medical Systems), or a PACS workstation. The embodiments can also be implemented in hardware. The embodiments can assist diagnosis by offering computer aided detection and quantification.

In an embodiment, the location of pulmonary embolisms (PEs) and the affected lung vessels can be automatically visualized and highlighted for convenient interactive inspection. The part of the pulmonary vessel tree which is "downstream" of the location of clots in the arteries is highlighted. In that way not only the location of the arterial clot but also the potentially endangered portion of the body is intuitively conveyed to the user.

A vascular structure may be represented by a three-dimensional dataset in which voxel values are assigned to voxels (volume elements). These voxels are associated with positions in 3D space, as is common in the art. The voxel values associated with the voxels are a derived from an output of a three-dimensional medical imaging modality such as CT or MR. In the case of CT, the voxel values usually are given in Hounsfield units (HU). Pulmonary embolisms often have Hounsfield values in the range of 0 to 100 HU, whereas vessels filled with intravenous contrast agent often have Hounsfield values in the range of 100 to 300 HU. This makes it possible to detect pulmonary embolisms by analyzing the dataset.

Figure 2:
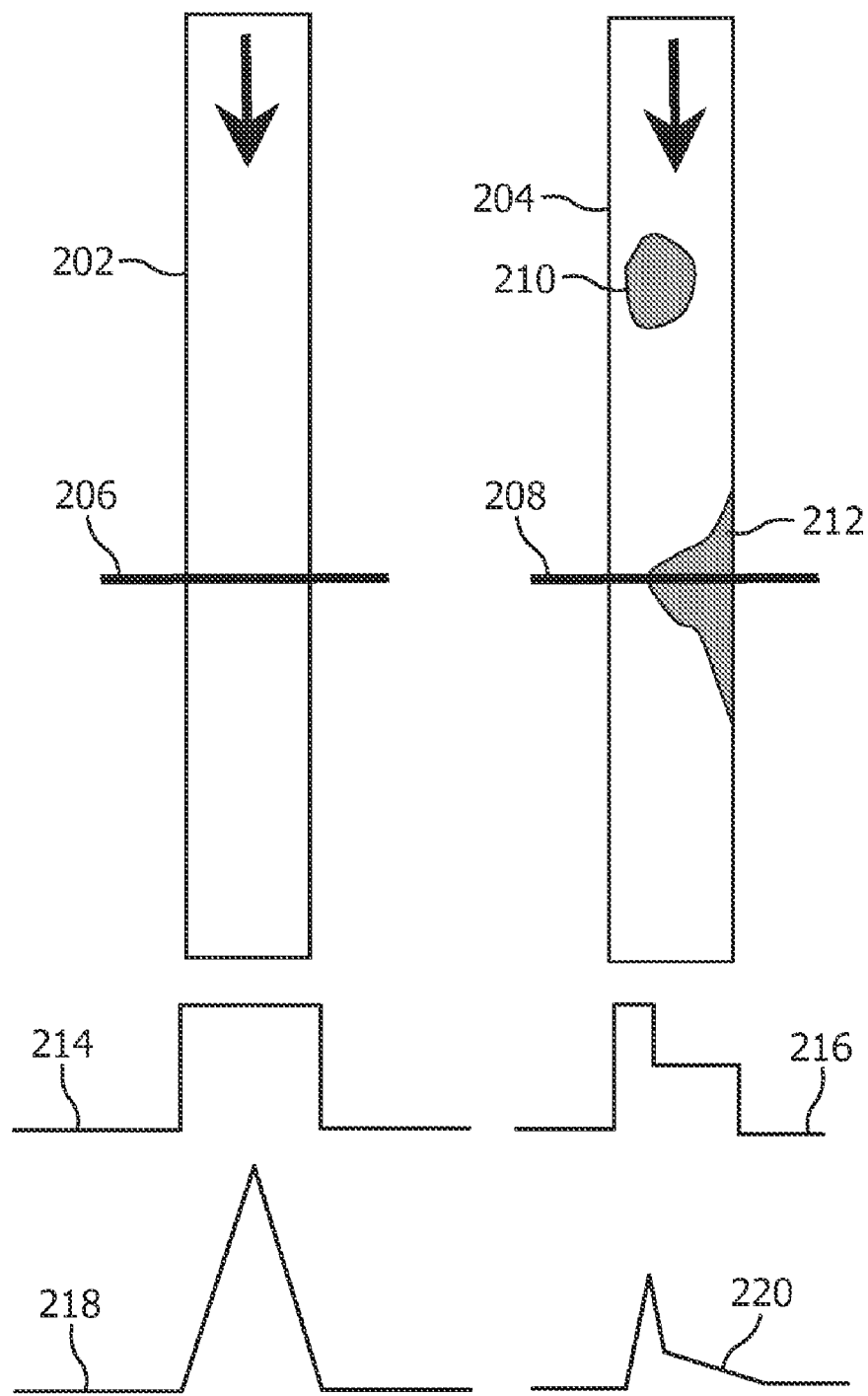
FIG. 2 is a diagram showing vessel structures and associated quantities.

FIG. 2 shows a simplified longitudinal cross section of two vessel segments that may occur in pulmonary arteries or other arteries. The arrows indicate the direction of flow of blood. Vessel segment 202 is not affected by pulmonary embolism. The figure shows only a simplified 2D representation of a tubular arterial structure. In practice, the dataset will be three-dimensional, and the cross section 206 is in reality a 2D plane intersecting the 3D vessel. The Hounsfield values measured along vessel cross section 206 are shown as a graph 214. In the ideal case, Hounsfield profile 214 is a step function with a high value inside the artery and a low value in the background (i.e., outside the artery). In practice, due to noise and scatter, the Hounsfield value profile will be less sharp. The background is defined as voxels below a certain Hounsfield unit threshold, such as −100 HU or 0 HU. Clots are typically at 0-100 HU, and contrast filled vessels at 100-300 HU.

The Figure also shows a graph 218 of the shortest path integral from the background corresponding to cross section 206. The shortest path integral for a point represents a smallest possible value obtained by integrating (in the discrete case: summing) the Hounsfield unit values on a path from anywhere in the background to that point. The shortest path integral can be used as a generalized distance map, because the distance map is defined as the length of a shortest path to the background and can be regarded as a special case of the generalized distance map by setting the Hounsfield values to 1.

The second vessel segment 204 shown in FIG. 2 comprises two clots 210 and 212. These clots are potentially pulmonary embolisms. Cross section 208 intersects clot 212 and the Hounsfield values corresponding thereto are displayed in graph 216. The corresponding generalized distance map is shown in graph 220. It can be observed, that the maximum of generalized distance map 220 corresponding to a clot is lower than the maximum of generalized distance map 218 corresponding to a healthy part of a vessel.

Figure 3A:
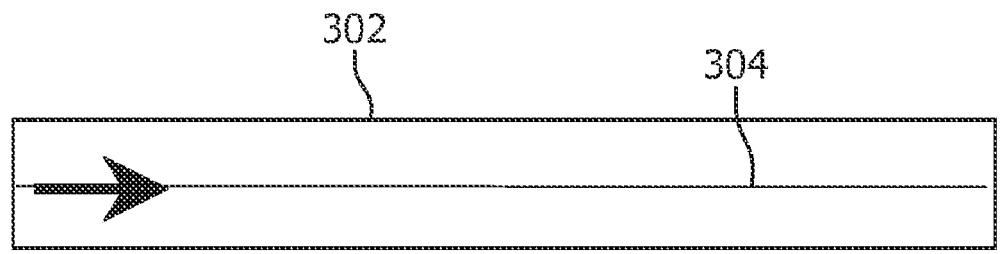
FIG. 3 is a diagram showing vessel structures and associated quantities.

FIG. 3a shows another view 302 of the vessel 202 without any clots. It has a vessel centerline 304 that corresponds to local maxima of the generalized distance map 218. Such a vessel centerline can be extracted in a way known in the art, using methods for finding a ridge line or crest line. Such a ridge line or crest line follows local maxima of the generalized distance map in the vessel. See for example "Initialization, noise, singularities, and scale in height ridge traversal for tubular object centerline extraction" by Aylward, S. R. and Bullitt, E., in IEEE Trans. Medical Imaging, Volume 21, Issue 2, 2002.

The value of the generalized distance map at this ridge line can be used as a measure of the amount of filling of the artery. It is especially well-suited for this purpose, as its value is lower not only when the vessel becomes thinner, but also when the measured Hounsfield unit values are generally smaller at a given point in the artery. Both these situations may be indicative of pulmonary embolism.

Figure 3B:
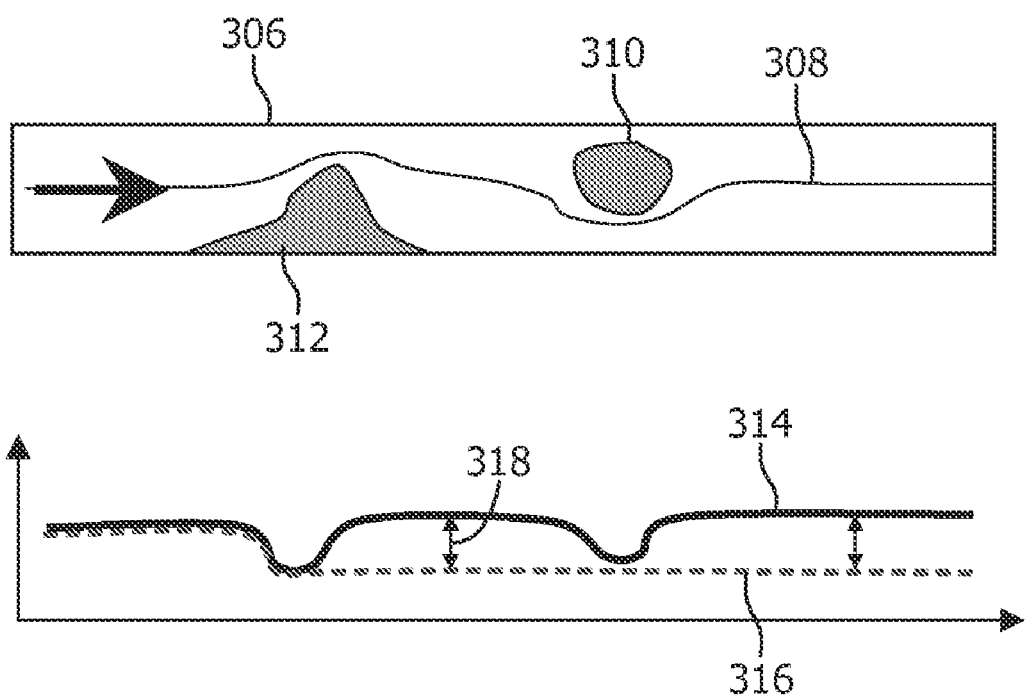

FIG. 3b shows another view 306 of the vessel 204 with clots 310 and 312. It shows the vessel centerline 308 computed as the ridge line of the generalized distance map. Graph 314 shows the values of the generalized distance map (as quantification of the filling) along ridge line 308. It shows local minima corresponding to clots 310 and 312. In a normal artery without clots, the filling is expected to be almost constant and to taper off slowly towards the distal parts of the arterial tree. At the location of a clot in the artery, the filling is lower, but will usually increase again downstream of (in other words, distal to) the clot. Dotted line 316 shows the minimal filling value encountered along the ridge line 308 when traversing from a proximal portion to a more distal portion of the vessel. The figure reveals a difference 318 between the minimal filling value 316 and the filling value 314 corresponding to the vessel portion distal to clot 312. This difference 318 may be used to assess the severity of the pulmonary embolism 312.

The difference 318 may be used to assess the severity of the pulmonary embolism 312 using quantitative analysis or using visual inspection. Other ways to use the difference 318 are also possible. The quantitative analysis could comprise integrating the difference values along vascular tree. This way, not only the difference value itself is taken into account, but also the extend of the arterial subtree whose blood inflow is obstructed by the clot. Visual inspection of pulmonary embolism may be facilitated by visualizing the difference 318. This can be done by varying a brightness, color, and/or texture of the vessels in dependence on the difference 318. Difference 318 is also referred to as "deficiency value".

Figure 4:
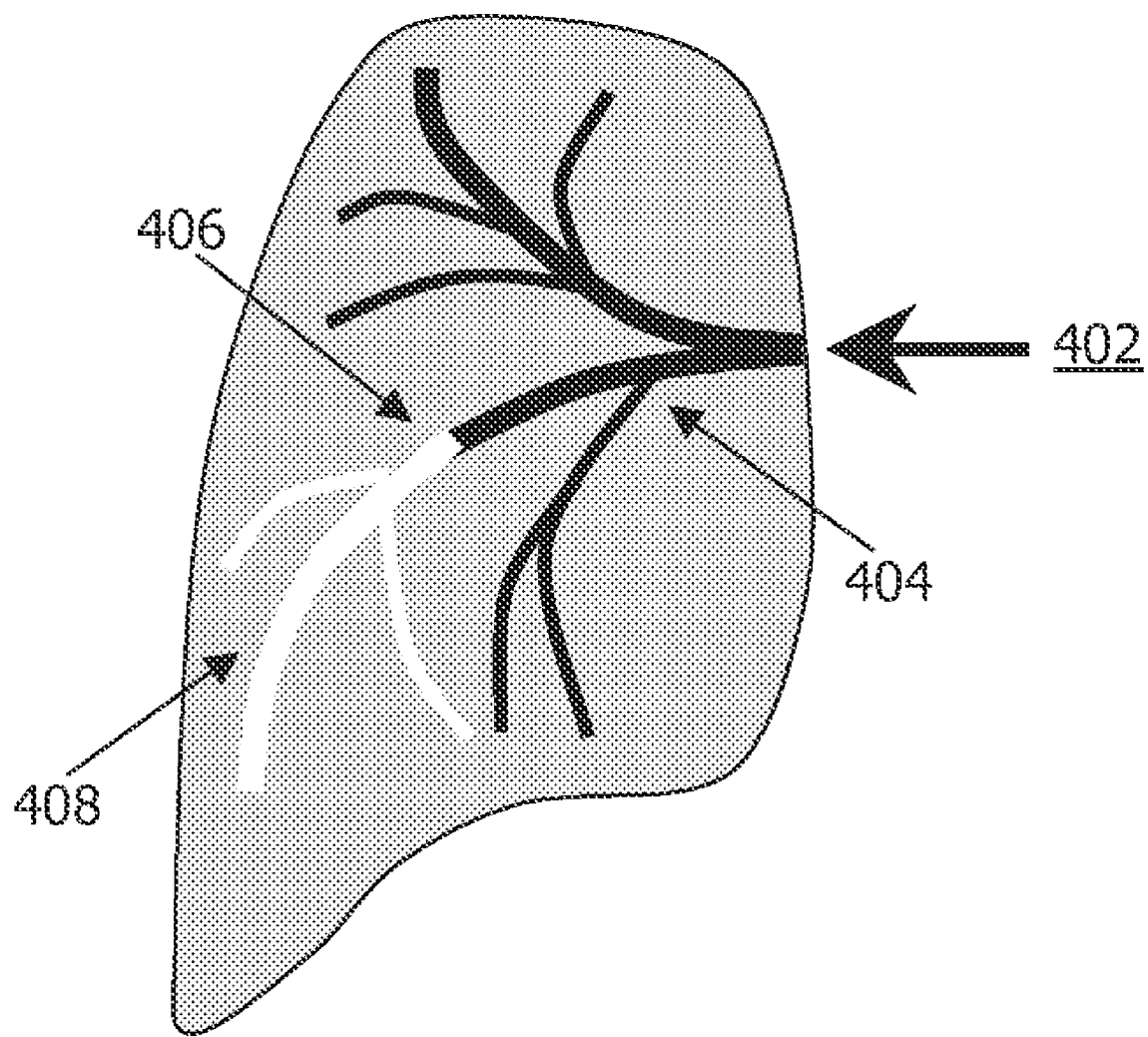
FIG. 4 is an illustration of a rendering of a vessel structure.

FIG. 4 is a schematic illustration of a rendering of pulmonary arteries within one lung. The most proximal vessel point is the blood inflow point 402. It is sometimes called a root point. The arteries 404 rendered in a dark way indicate a small difference 318, and the arteries 408 rendered in a bright way indicate a relatively large difference 318. The pulmonary embolism can be found at the transition point 406 where the artery's brightness changes. FIG. 4 is only a schematic illustration; in particular, rather than the binary "bright"/"dark" regions 404 and 408 in the figure, the rendering will usually have many more shades of gray corresponding to different values of the difference 318. This way of rendering allows an observer to judge the pulmonary embolism by considering both the value of the difference 318 and the size of the affected portion of the arterial tree.

The deficiency value 318 is preferably computed for all vessel voxels in the lung. The degree of the deficiency value 318 can be computed and displayed for the whole lung, or for example separately for the left and right lung or the separate lung lobes. It can also be shown numerically as percentages.

The degree of the deficiency value 318 can be visualized as a gray-value or color overlay over the CT images, where the color intensity corresponds to the deficiency value 318. A second visualization is computed as a maximum intensity projection (MIP) of the deficiency values (FIG. 4), where the deficiency value corresponds to brightness. The MIP may be computed in a coronal/sagittal direction. It can be computed and displayed for all possible angular directions (360 degrees), for example rotating around the z-axis of the data set. In this way, the severity of the PE locations and their extent can be appraised in one glance, and strong PEs cannot be overlooked due to their bright appearance in the MIP. Additionally, by clicking with a mouse curser (having for example the shape of a cross hair) on a PE shown in the MIP, a CT image viewer (e.g. an orthoviewer) is automatically set to display a CT slice view of the position in the CT dataset corresponding to the PE.

In an embodiment, the following steps are performed. First, the lung including the vessels is segmented. Second, the vascular structures are segmented for example using simple threshold segmentation. More advanced segmentation methods are known in the art and may be applied as well. The generalized distance map is computed for the segmented vascular structures using for example the shortest path integral. The distance transform may be used as well, although it does not take into account the actual Hounsfield values. Known algorithms such as the Dijkstra algorithm and/or fast marching methods may be used in this step. Third, one or more start seed points (most proximal points or inflow points) are identified in the main pulmonary artery (e.g. for left and right lung separately). This step may be performed manually or automatically using methods known in the art.

Fourth, the ridge line path is computed, starting from the seed point(s) and using the generalized distance map. Known efficient methods include priority-queue region-growing and fast-marching methods. Fifth, the vessels are processed, starting with the inflow point(s) and traversing in a downstream direction along the ridge line(s). In this step a difference (or for example a ratio) is computed between the value of the generalized distance map at the current point and the minimum encountered on the path so far. For example, a relatively high intensity is given in case of a relatively large difference. Also, an intensity value is computed for each computed difference value, using for example an affine transformation or a look-up table. Sixth, a maximum intensity projection (MIP) and a corresponding depth-map are computed from the given intensities. This way, a mouse click on a rendering of the MIP image can be associated with the corresponding location in the original CT data volume using the depth-map. It allows a user friendly way of navigating through the CT data volume.

Figure 5:
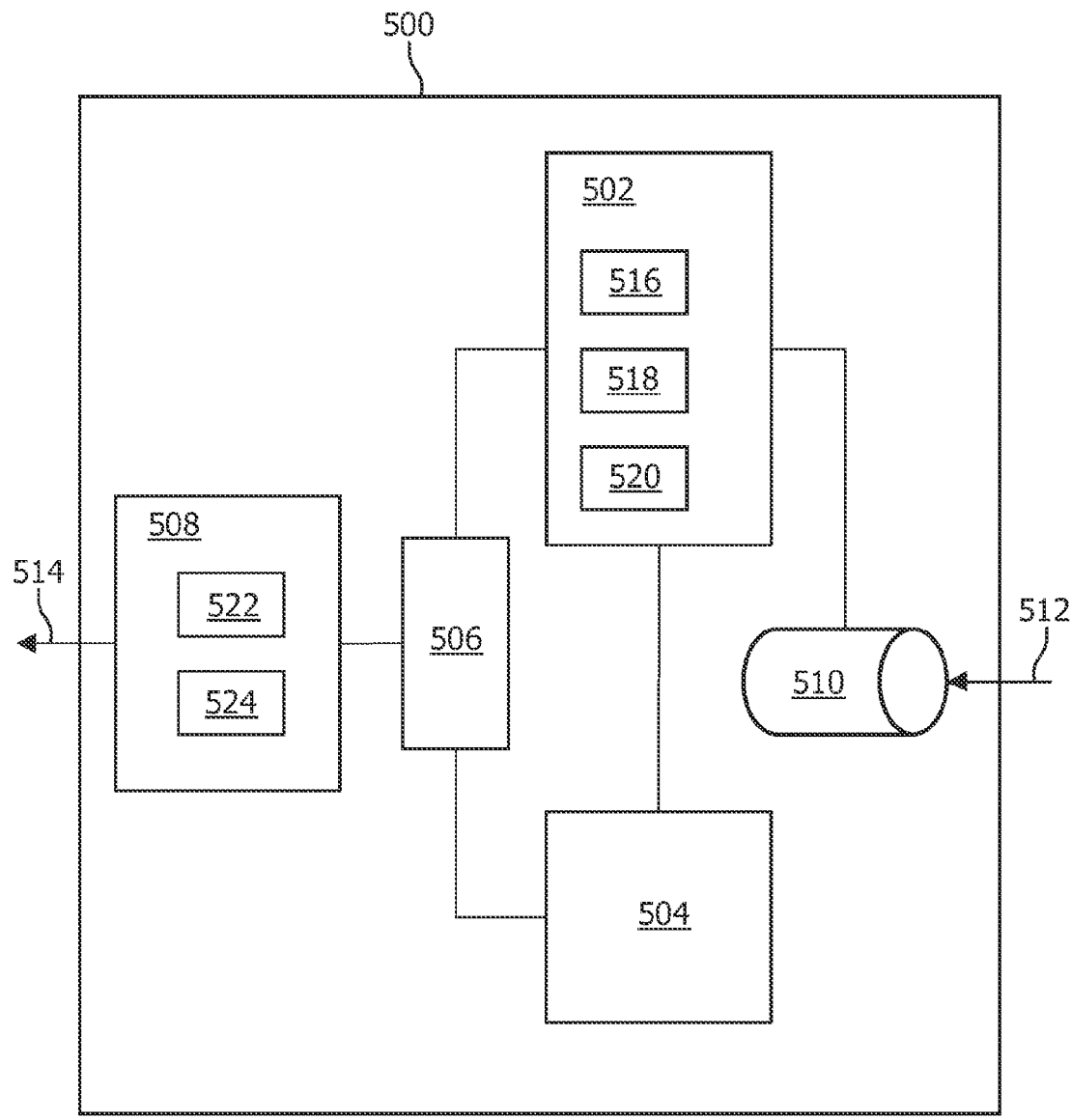
FIG. 5 is a diagram of an embodiment.

FIG. 5 shows an embodiment. It shows an apparatus, for example a backend of a CT or MR scanner. The apparatus may also be a medical workstation. The apparatus has an input 512 to receive a three-dimensional dataset and a storage 510 for storing the dataset. The three-dimensional dataset associates voxel values with voxels. Each voxel represents a volume element at a predefined spatial location. The voxel value may represent a Hounsfield unit value or any other quantity that can be derived from measurements. If the scanner is an MR scanner, the voxel value represents an MR-related quantity. The quantity is indicative of an amount of blood flowing through a vessel. Optionally this may be measured using a contrast agent flowing through the vessel. The apparatus comprises a means (502) for computing filling values. These filling values are derived from the voxel values in such a way that a single filling value describes the degree of filling of a vessel cross section. These filling values may be computed for each vessel cross section. For example a generalized distance map may be employed as discussed above. This step may also include extracting a structure of the vessel tree, i.e., finding the inflow point, the vessel centerline (ridge line), and the bifurcation points of the vessels.

The figure also shows a means 504 for finding local minima of the filling values. Here, the filling value is seen as a function of the position along the central axes. A local minimum may indicate an embolism. A minimum filling value is associated with a position in the vascular structure, for example a vessel cross section or a ridge point, where the minimum filling value is defined to be the smallest filling value on the path along the vascular structure upstream of that position.

The figure also shows a means 506 for computing deficiency values. A deficiency value is associated with a position along the vascular structure (for example a vessel cross section or equivalently a ridge point) and is indicative of a difference between the filling value associated with the position and the minimum filling value associated with the position. This value represents the (potential) severity of embolism(s) or vessel narrowing(s) that can be found proximal to the position.

The deficiency values are the basis for output signal 514. Quantitative and qualitative information about the deficiency values may be provided to output 514. Renderings of the 3D dataset using the deficiency values to apply different colors or brightness values depending on the deficiency values can be provided to output 514. Also, integrated values of the deficiency may be computed and provided to output 514. The deficiency values may be subject to further processing or provided to output 514 in a raw format.

In an embodiment, the means 502 for computing the filling values comprises means 516 for computing a generalized distance map associating respective generalized distance values with respective voxels based on the voxel values, means 518 for identifying respective ridge voxels on a ridge line of the generalized distance map, and means 520 for establishing the respective filling values based on the respective generalized distance values associated with the respective identified ridge voxels.

In an embodiment, output 514 is provided by rendering means 508. Rendering means 508 stores a mapping 522 associating respective deficiency values with respective rendering parameters such as intensities or colors or textures, and a means 524 for applying the parameters according to the mapping when rendering a portion of the vessel at or around a position in the vascular structure for which a deficiency value is available. This way, portions of the vascular structure associated with the same deficiency value are rendered with the same rendering parameters.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. The carrier may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system (500) for visualizing a vascular structure (306) represented by a three-dimensional dataset in which respective voxel values are associated with respective voxels, the system comprising:
    means (502) for establishing respective filling values (314), based on the voxel values, associated with respective positions in the vascular structure, a respective filling value being indicative of an amount of blood in a neighborhood of the respective position in the vascular structure;
    means (504) for determining respective minimum filling values (316) associated with the respective positions in the vascular structure, a respective minimum filling value being a minimum of the filling values (314) associated with positions upstream of a respective position;
    means (506) for computing respective deficiency values (318) associated with the respective positions in the vascular structure, a respective deficiency value being computed in dependence on the filling value (314) associated with the respective position and the minimum filling value (316) associated with the respective position; and
    an output (514) for providing a visualization (408) in dependence on the deficiency values.

2. The system according to claim 1, wherein the means for establishing the respective filling values comprises:
    means (516) for computing a generalized distance map in which respective generalized distance values based on the voxel values are associated with respective voxels; and
    means (518) for establishing a vessel centerline in dependence on the generalized distance map or in dependence on the voxel values;
    means (520) for establishing the respective filling values in dependence on the respective generalized distance values associated with the respective voxels at the vessel centerline.

3. The system according to claim 2, wherein the means for establishing the vessel centerline comprises:
    means for identifying a plurality of voxels on a crest line of the generalized distance map or of the voxel values; and
    is arranged for using the plurality of voxels as the vessel centerline.

4. The system according to claim 1, wherein the voxel values are indicative of a local concentration of contrast agent, and the means for establishing the respective filling values is arranged for computing the respective filling value as an estimate of a degree of local contrast agent filling in a cross section of the vessel at the respective position in the vascular structure.

5. The system according to claim 1, wherein the means for identifying respective minimum filling values comprises means for establishing the positions upstream of the respective position by identifying positions along the vascular structure between the respective position and a predefined inflow point of the vascular structure.

6. The system according to claim 1, wherein the means for computing the respective deficiency values is arranged for computing the respective deficiency value in dependence on a difference between the filling value associated with the respective position and the minimum filling value associated with the respective position.

7. The system according to claim 1, further comprising a rendering means (508) for rendering the three-dimensional dataset on a display in dependence on the computed deficiency values, the rendering means comprising:
    a storage for storing a mapping (522) associating respective deficiency values with respective rendering parameters;
    means (524) for applying the parameters according to the mapping and the deficiency values.

8. A method of visualizing a vascular structure (306) represented by a three-dimensional dataset in which respective voxel values are associated with respective voxels, the method comprising:
    establishing respective filling values (314), based on the voxel values, associated with respective positions in the vascular structure, a respective filling value being indicative of an amount of blood in a neighborhood of the respective position in the vascular structure;
    determining respective minimum filling values (316) associated with the respective positions in the vascular structure, a respective minimum filling value being a minimum of the filling values (314) associated with positions upstream of a respective position;
    computing respective deficiency values (318) associated with the respective positions in the vascular structure, a respective deficiency value being computed in dependence on the filling value (314) associated with the respective position and the minimum filling value (316) associated with the respective position; and
    providing a visualization (408) in dependence on the deficiency values.

* * * * *